United States Patent
Manico et al.

(10) Patent No.: US 6,527,700 B1
(45) Date of Patent: Mar. 4, 2003

(54) MANAGEMENT OF PHYSIOLOGICAL AND PSYCHOLOGICAL STATE OF AN INDIVIDUAL USING BIOPHILIC IMAGES

(76) Inventors: Joseph A. Manico, Eastman Kodak Company, 343 State St., Rochester, NY (US) 14650; Tomasz A. Matraszek, Eastman Kodak Company, 343 State St., Rochester, NY (US) 14650; Girish V. Prabhu, Eastman Kodak Company, 343 State St., Rochester, NY (US) 14650

(*) Notice: Subject to any disclaimer, the term of this patent is extended or adjusted under 35 U.S.C. 154(b) by 0 days.

(21) Appl. No.: 09/712,745

(22) Filed: Nov. 14, 2000

Related U.S. Application Data

(63) Continuation-in-part of application No. 09/430,580, filed on Oct. 20, 1999.

(51) Int. Cl.[7] ............................................. A61M 21/00
(52) U.S. Cl. ........................... 600/26; 600/27; 600/545; 434/236
(58) Field of Search ........................... 600/26, 27, 544, 600/545, 301; 434/236, 237, 238

(56) References Cited

U.S. PATENT DOCUMENTS

| | | |
|---|---|---|
| 3,855,998 A | 12/1974 | Hidalgo-Briceno |
| 4,632,126 A | 12/1986 | Aguilar |
| 5,047,930 A | 9/1991 | Martens et al. |
| 5,253,168 A | 10/1993 | Berg |
| 5,304,112 A | 4/1994 | Mrklas et al. |
| 5,343,871 A | 9/1994 | Bittman et al. |
| 5,465,729 A | 11/1995 | Bittman et al. |
| 5,596,994 A | 1/1997 | Bro |
| 5,676,138 A | 10/1997 | Zawilinski |

OTHER PUBLICATIONS

Affective Judgement and Psychophysiological Response: Dimensional Covariation in the Elevation of Pictorial Stimuli, by: Greenwald, Cook and Lang, Journal of Pyschophysiology 3 (1989), pp. 51–64.

Remembering Pictures: Pleasures and Arousal in Memory, by: Bradley, Greenwald, Petry and Lang: Journal of Experimental Psychology, Learning and Cognition; 1992, vol. 18, No. 2, pp. 379–390.

Looking at Pictures: Affective, Facial, Visceral, and Behavioral Reactions; by: Lang, Greenwald, Bradley and Hamm, Psychophysiology, 30 (1993), pp. 261–273.

Picture Media and Emotion: Effects of a Sustained Affective Context; by: Bradley, Cuthbert, and Lang, Psychophysiology, 33 (1996), pp. 662–670.

Emotional Arousal and Activation of the Visual Cortex: An fMRI Analysis: by: Lang, Bradley, Fitzsimmons, Cuthbert, Scott, Bradley, Moulder, and Nangia, Psychophysiology, 25 (1998), pp. 199–210.

*Primary Examiner*—Rosiland S. Kearney

(57) ABSTRACT

An apparatus for managing the physiological and/or psychological state of an individual comprising a source of biophilic images; a device for sensing at least one physiological parameter of an individual; and a display, linked to said source and said device, for displaying biophilic images from said source as a function of the sensed physiological parameter in order to manage a physiological or psychological state of the individual.

13 Claims, 6 Drawing Sheets

MANAGEMENT OF PHYSIOLOGICAL AND PSYCHOLOGICAL STATE OF AN INDIVIDUAL USING BIOPHILIC IMAGES

CROSS REFERENCE TO RELATED APPLICATIONS

This application is a Continuation-in-part of U.S. patent application Ser. No. 09/430,580, filed Oct. 20, 1999, inventors Prahbu et al., titled Management of Physiological and Psychological State Of An Individual Using Images—Overall System.

FIELD OF THE INVENTION

This invention relates in general to the management of a physiological and/or psychological state of an individual and more particularly to the management of the physiological and/or psychological state of an individual through the use of biophilic images as a function of a sensed physiological parameter of an individual viewing the images.

BACKGROUND OF THE INVENTION

The physical, emotional and mental well-being of an individual can contribute greatly to the quality of life of that individual. In our hyperactive, hyperkinetic world, stress results in numerous physical reactions, such as, headache, muscle tension, dizziness or sleeplessness, weight gain, chronic coughing, nervous ticks, stomach upset and shortness of breath. Job stress alone is estimated to cost American business $300,000,000,000 annually. Stress is the response of the body and/or mind to a demand placed upon it. Stress can be caused by major events in one's life, such as, death of a loved one, marital breakup, personal injury or sickness, and job loss. Stress can also result from our day-to-day hectic style of living, where one attempts to excel simultaneously at being a super employee, a super parent, a super spouse, and a super citizen. Unless chronic stress is controlled, one puts oneself at risk for a host of serious problems, such as, heart disease, stroke, migraines, muscle and nerve disorders.

The typical path to obtain relief from stress is to visit one's doctor. Stress conditions result in up to 70% of all doctor's visits. Typically, drugs are prescribed to relieve stress. One stress reducing medication alone accounts for $6,000,000 per day in sales. Thus, alternative approaches to traditional medicine have become increasingly popular. Resort to Eastern religions, transcendental meditation, and biofeedback techniques have been proposed to empower the individual to reduce stress without the potential deleterious effects of powerful and expensive prescription drugs or invasive surgery.

It has been proposed to use images for the purpose of optimizing one's physiological and psychological state. There are several reasons for this.

(1) It has been shown that one can measure a reliable physiological response for images that differ in valence and arousal. It has been demonstrated that images rated differently with respect to perceived activation and pleasantness elicited physiological responses of different magnitude. Thus, magnitude of the skin conductance response correlated with perceived arousal level produced by pictorial stimuli. At the same time heart rate acceleration during first 4 to 5 seconds of image presentation reflected "valence" or degree of perceived pleasantness of an image. Other physiological parameters that reflect an individual's physiological reactions to images have also been demonstrated. These results imply that, for an individual viewer, images can potentially be classified based on one's physiological reactions in terms of emotional arousal.

(2) Imagery is known to be able to change a person's state. Paintings, movies, pictures are constantly affecting our mood and performance level. Power of visualization and affective content determine effective use of imagery in therapeutic sessions. Experimental research has also shown that presentation of images of similar content may cause significant shifts in physiological reactions.

(3) Digital imaging technology provides an almost instant access to image databases through the internet. Moreover, the potentially unlimited degree of digital manipulation makes images very attractive means of interaction and communication. Images can be easily transformed to alter or enhance people's preferences, i. e., for hue, saturation, depth, aesthetic feelings, etc. Image transformation by itself can provide biofeedback information to the user to facilitate learning how to control one's physiological and emotional state, e. g., stress.

Following are several proposals to use images as a means of changing one's state that have not proven to be entirely successful.

U.S. Pat. No. 5,465,729, issued Nov. 14, 1995, inventors Bittman et al. and U.S. Pat. No. 5,343,871, issued Sep. 6, 1994, inventors Bittman et al., disclose the use of measurements of electrophysiological quantities to control a presentation to a subject of a series of prestored audio-visual sequences.

U.S. Pat. No. 3,855,998, issued Dec. 24, 1974, inventor Hidalgo-Briceno discloses an entertainment device that includes sensing means connected to the user for sensing galvanic skin response and brain theta waves. According to a given measured state of a user the device provides a given type of predetermined audio-visual stimulation to the user for a timed interval to hold one in or move one toward a desired state. At the end of the interval, the user's state is again measured and a further timed audio-visual response according to the measured state is presented to the user.

U.S. Pat. No. 5,596,994, issued Jan. 28, 1997, inventor Bro, discloses an automated and interactive positive motivation system that allows a health care professional to produce and send a series of motivational messages to a client to change or reinforce a specific behavioral pattern.

U.S. Pat. No. 5,304,112, issued Apr. 19, 1994, inventors Mrklas et al., discloses an integrated stress reduction system which detects the stress level of a subject and displays a light pattern reflecting the relationship between the subject's stress level and a target level. The system also provides relaxing visual, audio, tactile, environmental, and other effects to aid the subject in reducing one's stress level to the target level.

U.S. Pat. No. 4,632,126, issued Dec. 30, 1986, inventor Aguilar, discloses a biofeedback technique which permits simultaneous, preferably redundant, visual and auditory presentation on a color TV of any intrinsically motivating stimuli together with continuous information pertaining to the physiological parameter to be controlled. As the subject changes a certain physiological parameter, the image and sound become clearer if the change occurs in the desired direction.

U.S. Pat. No. 5,253,168, issued Oct. 12, 1993, inventor Berg, discloses a system for allowing an individual to express one's self in a creative manner by using biofeedback signals to direct imaging and audio devices.

U.S. Pat. No. 5,676,138, issued Oct. 14, 1997, inventor Zawalinski, discloses a multimedia computerized system for detecting emotional responses of human beings and changes thereof over time.

U.S. Pat. No. 5,047,930, issued Sep. 10, 1991, inventors Marten, et al., discloses methods of analyzing physiological signals from a subject and analyzing them using pattern recognition techniques to determine a particular sleep state of the subject. Use of any associated feedbacks is not disclosed.

The following papers discuss various emotional responses and physiological responses of subjects to viewing images.

Affective judgement and psychophysiological response: dimensional covariation in the evaluation of pictorial stimuli; by: Greenwald, Cook and Lang; Journal of Pyschophysiology 3 (1989), pages 51–64.

Remembering Pictures: Pleasure and Arousal in Memory, by: Bradley, Greenwald, Petry and Lang; Journal of Experimental Psychology, Learning Memory and Cognition; 1992, Vol. 18, No. 2, pages 379–390.

Looking at Pictures: Affective, facial, visceral, and behavioral reactions; by: Lang, Greenwald, Bradley, and Hamm, Psychophysiology, 30 (1993), pages 261–273.

Picture media and emotion: Effects of a sustained affective context; by: Bradley, Cuthbert, and Lang, Psychophysiology, 33 (1996), pages 62–670.

Emotional arousal and activation of the visual cortex: An fMRI analysis; by: Lang, Bradley, Fitzsimmons, Cuthbert, Scott, Bradley, Moulder, and Nangia; Psychophysiology, 25 (1998), pages 199–210.

The techniques disclosed in the above references have the following disadvantages.

1. Known biofeedback techniques require expensive equipment, a trained instructor, and individual training in order to realize the benefits from the techniques.

2. Known biofeedback techniques that use sounds, icons, or indicators that react to a user's physical or mental state have been ineffective in inducing or encouraging a relaxed state in the user.

SUMMARY OF THE INVENTION

According to the present invention, there is provided a solution to the problems of the prior art.

According to a feature of the present invention, there is provided an apparatus for managing the physiological and/or psychological state of an individual comprising a source of biophilic images; a device for sensing at least one physiological parameter of an individual; and a display, linked to said source and said device, for displaying biophilic images from said source as a function of the sensed physiological parameter in order to manage a physiological or psychological state of the individual.

It is therefore desirable to provide an improved system that would incorporate biophilic images that respond to the user's mental, physical and physiological state via biofeedback techniques. A simple example of this would be a time-lapse image of a flower budding. The user's monitored physical and mental state would control the time-lapse sequence. As the user became relaxed the rate at which the "budding process" progressed would accelerate. This would provide a non-abstract, non-distracting means to monitor one's own physical and mental state while providing images that induce and encourage relaxation.

ADVANTAGEOUS EFFECT OF THE INVENTION

The invention has the following advantages.

1. A non-distracting means is provided to monitor one's own mental and physical state.

2. Images are used that indicate the status of user's mental and physical state and that also induce and encourage change of physiological and psychological state in a desired direction, e.g., relaxation.

3. A more effective biofeedback technique.

4. A more intuitive biofeedback technique.

5. A dual methodology of using relaxing biophilic image sequences which are controlled by biofeedback.

DETAILED DESCRIPTION OF THE INVENTION

In general, the present invention relates to the management of a physiological and/or psychological state of an individual through the use of biophilic images. Biofeedback has been shown to be an effective means to manage stress. Real world images of fruit, flowers placed in water, contained fire, park-like settings (open green area with scattered trees) and sunsets have been shown to induce relaxation. This effect is called biophilia.

The biophilia hypothesis asserts the existence of a biologically based, inherent human need to affiliate with life and life-like processes. This proposition suggests that human identity and personal fulfillment somehow depend on our relationship to nature. The human need for nature is linked not just to the material exploitation of the environment, but also to the influence of the natural world on our emotional, cognitive, aesthetic, and even spiritual development. Even the tendency to avoid, reject, and at times, destroy elements of the natural world can be viewed as an extension of an innate need to relate deeply and intimately with the vast spectrum of life about us.

The hypothesis suggests that the widest valuational affiliation with life and life-like processes (ecological functions and structures, for example) has conferred distinctive advantages in the human evolutionary struggle to adapt, persist, and thrive as individuals and as a species. Conversely, this notion intimates that the degradation of this human dependence on nature brings the increased likelihood of a deprived and diminished existence again, not just materially, but also in a wide variety of affective, cognitive, and evaluative respects. The biophilia notion, therefore, powerfully asserts that much of the human search for a coherent and fulfilling existence is intimately dependent upon our relationship to nature.

Figure 1:
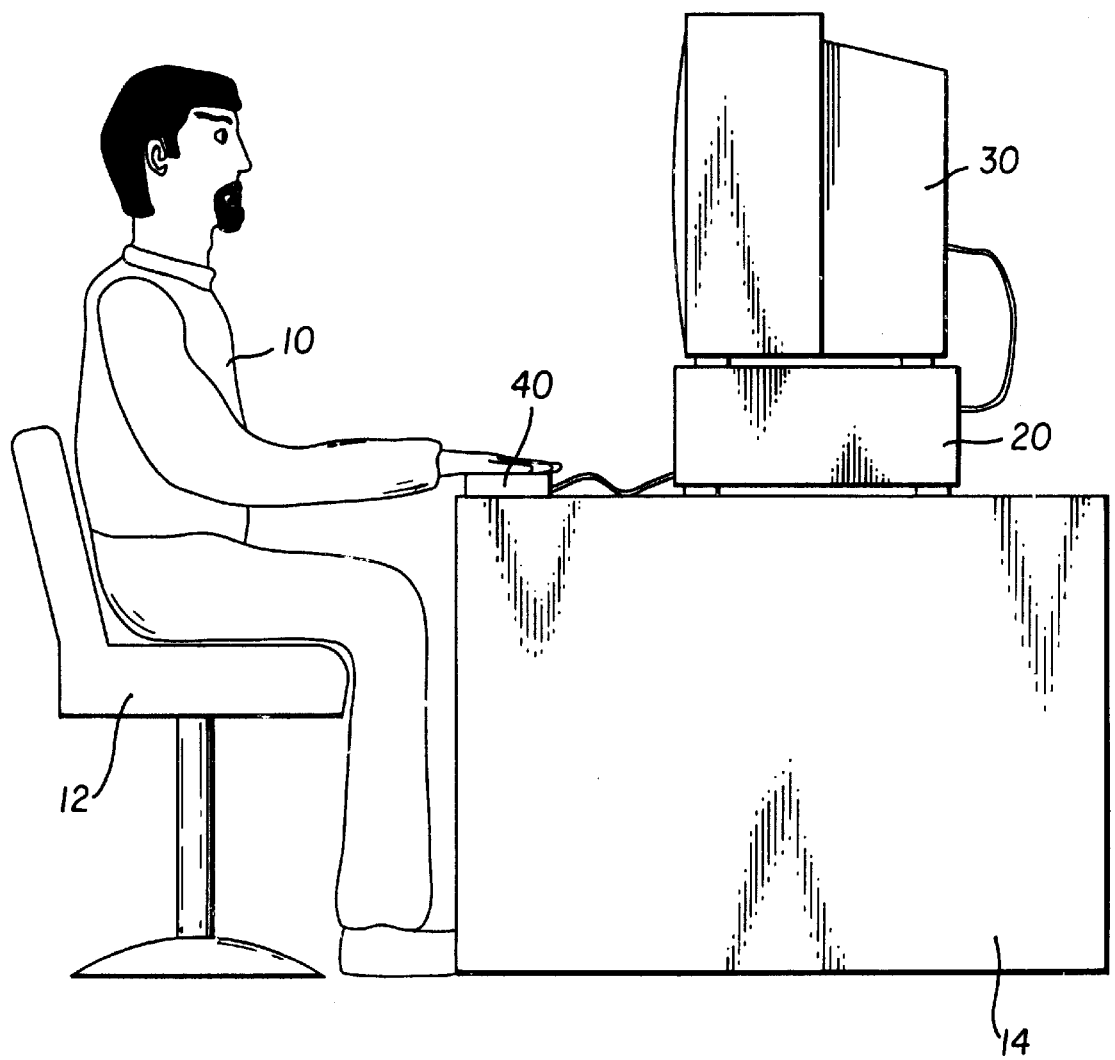
FIG. 1 is a graphical representation of a user viewing images on a computer screen while in contact with a physiology monitoring device.

According to the invention, biophilic images are displayed to an individual in response (biofeedback) to sensed physiological parameter(s) of the individual in order to assist the individual in managing a physiological or physical state. Referring to FIG. 1, there is shown implementation of the present invention.

As shown, an individual user 10 is seated in chair 12 before a table 14. Table 14 supports a computer 20 having a computer monitor display 30. A physiology 20 monitoring device 40 is connected to computer 20. Device 40 senses a physiological parameter of individual user 10. As shown, the hand 16 of user 10 is resting on device 40. The physiological parameter sensed can be one or more of the following, heart rate, body temperature (peripheral, core), blood pressure, skin conductance response, brain waves, electromyography, eye saccades, etc. The sensed physiological parameter provides a biofeedback signal to computer 30 to display biophilic images on display 30. The displayed images are stored in memory in computer 30.

The generation of suitable biophilic image sequence can be achieved by making time-lapse image sequences of the following natural events:

Flowers budding and blooming.

Flowers budding, blooming and dying.

The surface of a body of water progressing from "rippled" to "still".

Waves dissipating until the body of water becomes still rain falling on a body of water decreasing in intensity until the water becomes still.

A contained fire with increasing intensity.

A contained fire with decreasing intensity.

Clouds dissipating in a clear sky.

Clouds forming in a clear sky.

Figure 2A:
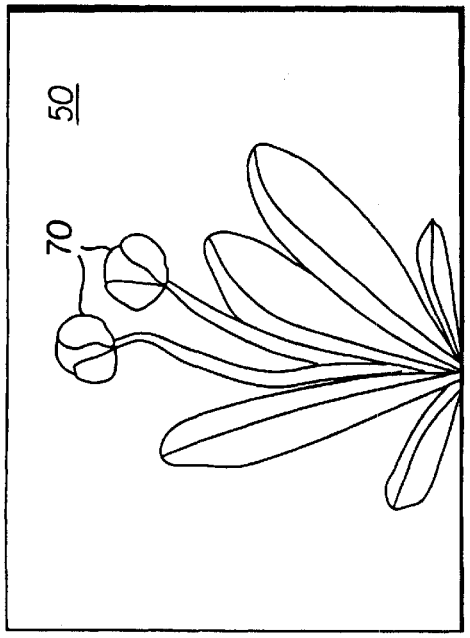
FIGS. 2a–2f are graphical representations of a series of images depicting flowers blooming. The images progress from FIG. (2a) showing closed flower "buds" to FIG. (2f) showing the same flowers in full bloom. These images are a subset of the actual number incremental images which may be in the thousands.
Figure 2B:
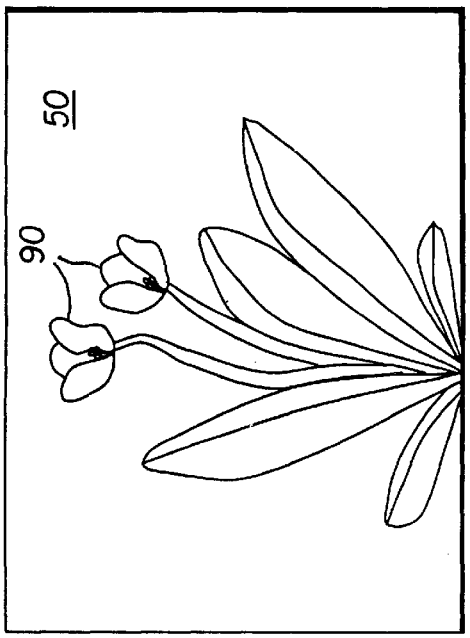
Figure 2C:
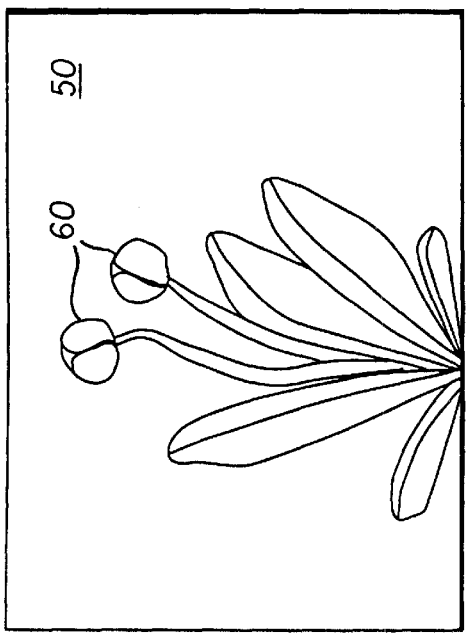
Figure 2D:
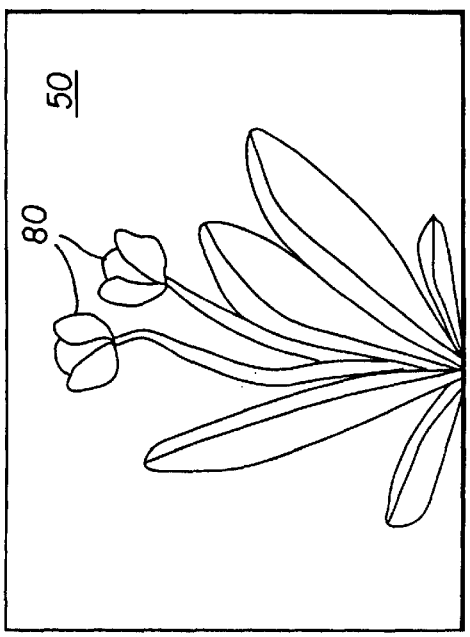
Figure 2E:
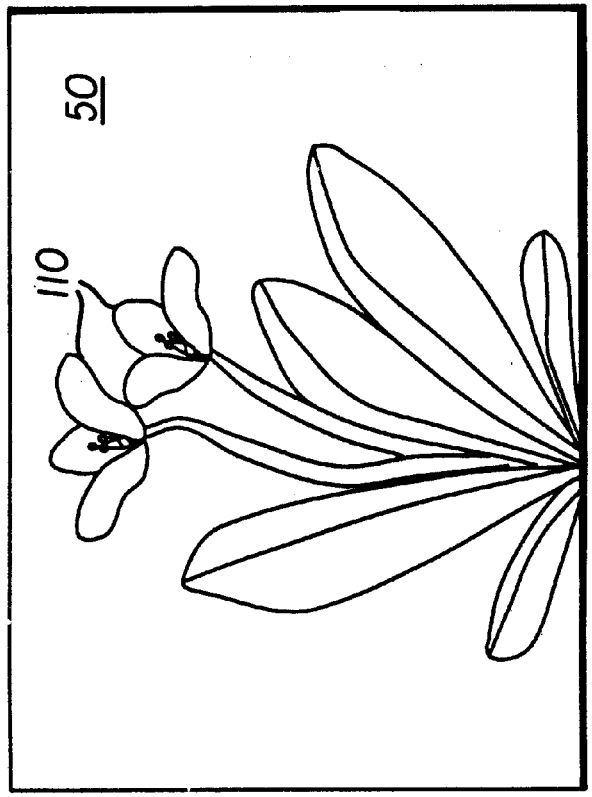
Figure 2F:
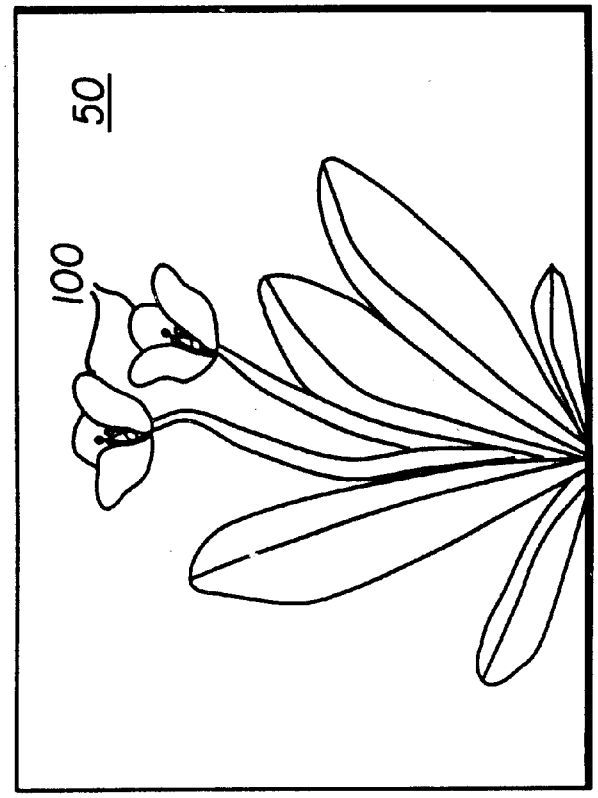

FIGS. 2a–2f illustrate a series of time lapse biophilic images depicting a flower blooming. The images 60–110 respectively progress from FIG. 2a showing closed flower buds to FIG. 2f showing the same flowers in full bloom. These images are a subset of the actual number of incremental images which may be in the thousands.

Figure 3A:
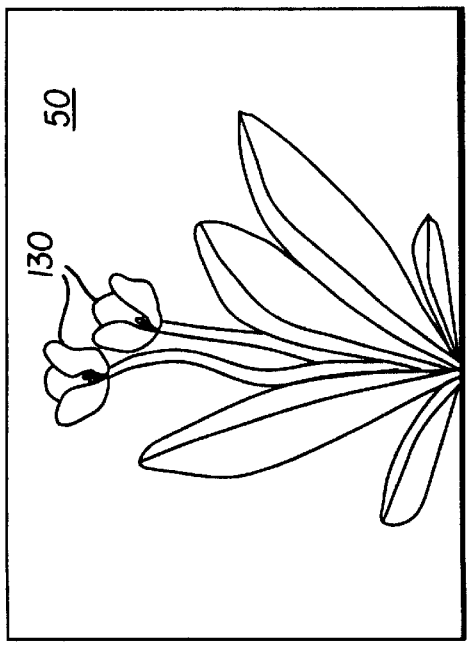
FIGS. 3a–3f are graphical representations of a series of images depicting flowers in motion. The images progress from FIG. (3a) showing flowers leaning toward the right side of the frame to FIG. (3d) showing the same flowers leaning toward the left side of the frame and FIG. (3f) showing the same flowers back in their original location on the right side of the frame. These images are a subset of the actual number incremental images which may be in the thousands.
Figure 3B:
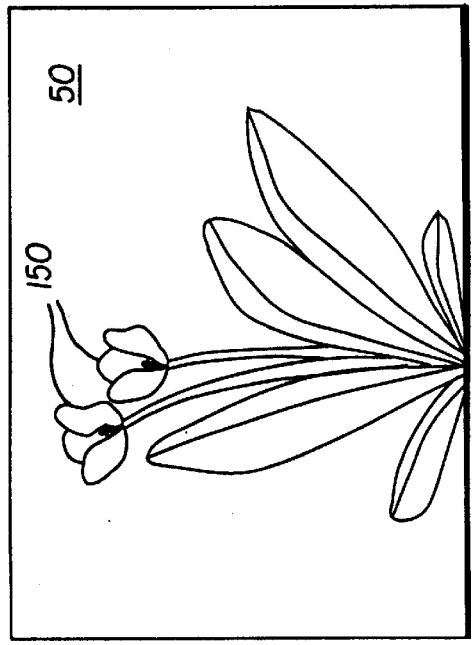
Figure 3C:
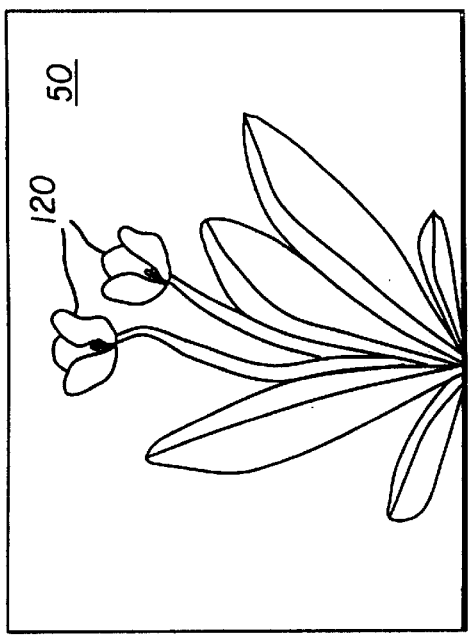
Figure 3D:
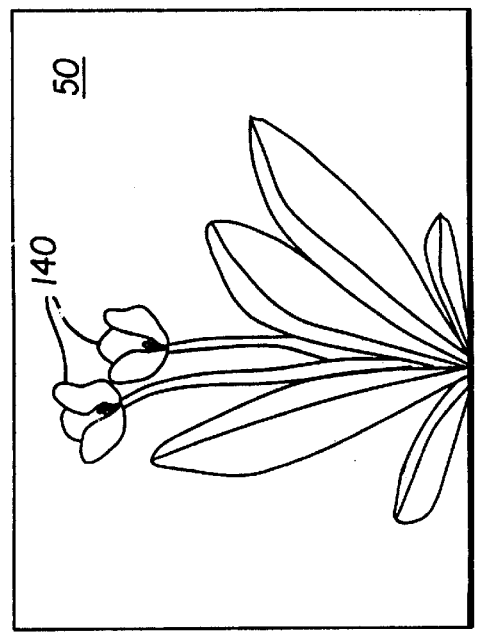
Figure 3E:
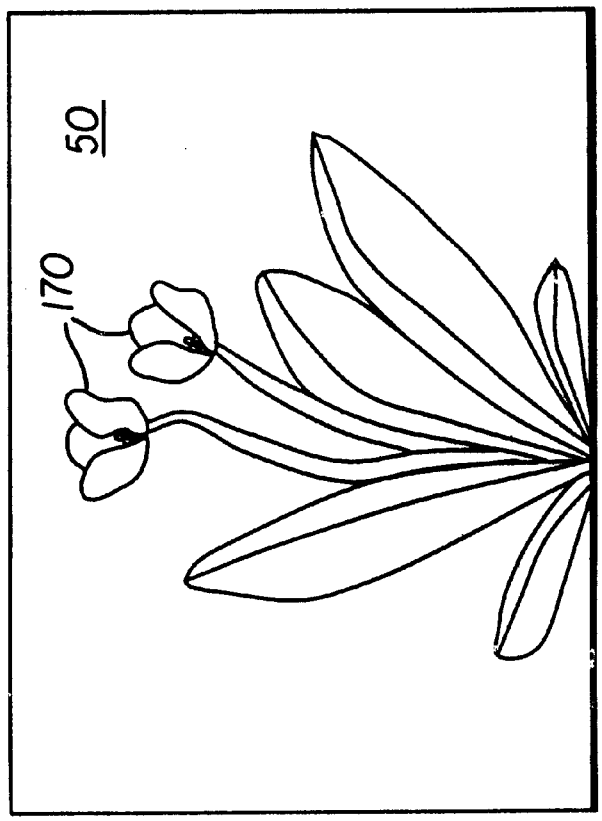
Figure 3F:
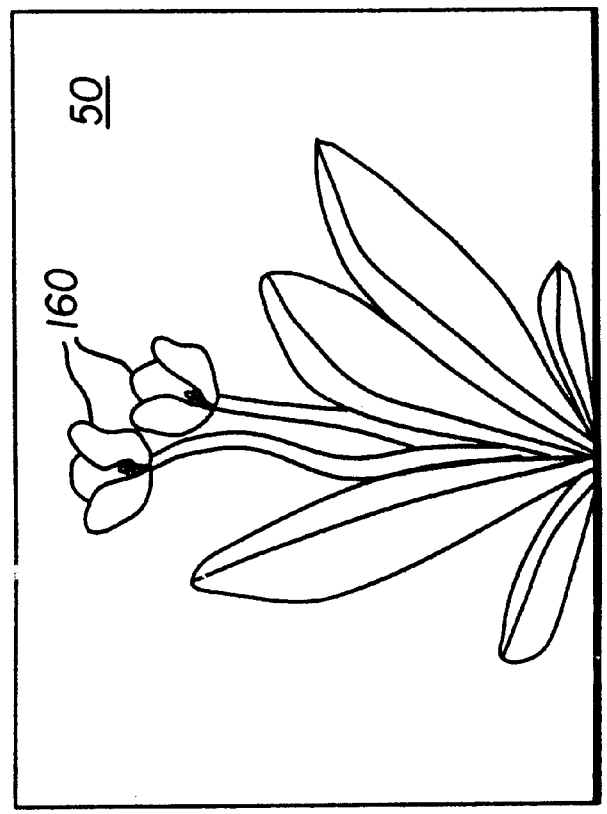

FIGS. 3a–3f illustrate another series of time lapse biophilic images depicting flowers in motion. The images 120–170 respectively progress from FIG. 3a showing flowers leaning toward the right side of the frame to FIG. 3d showing the same flowers leaning toward the left side of the frame and to FIG. 3f showing the same flowers back in their original location on the right side of the frame. These images are a subset of the actual number of incremental images which may be in the thousands.

The biophilic images are typically a sequence of scenes from nature that are photographed, digitized and stored in memory. The images can also be created using computer graphical techniques which can produce remarkably life-like scenes. The images can be stored in removable computer storage media such as optical disk or tape, magnetic disk or tape, memory card, or the like. The images can also be stored in a location remote from computer 20 and transmitted to computer 20 by known wireless and wired telecommunication systems (internet, intranet, public telephone network, cable, satellite).

Figure 4:
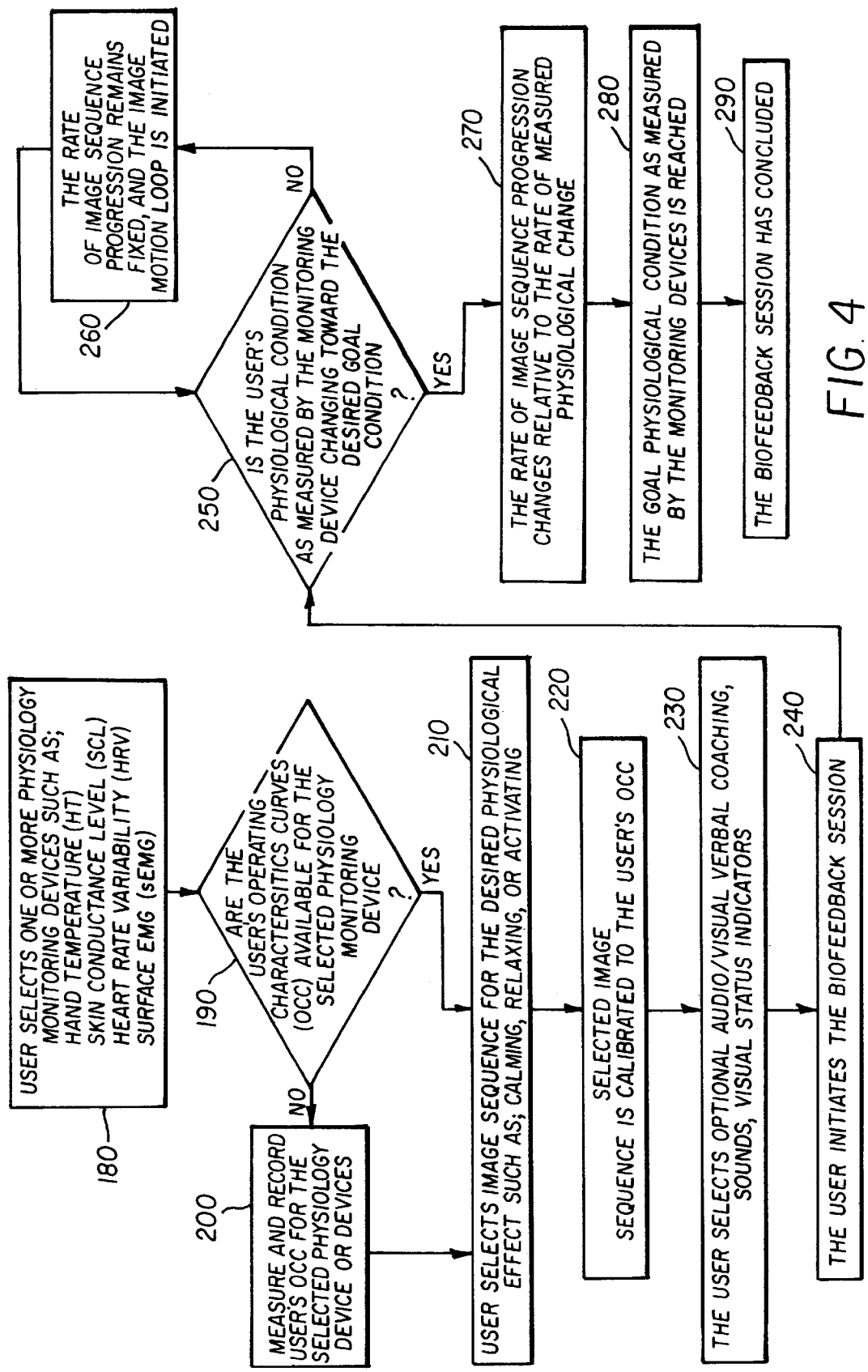
FIG. 4 is a flow chart documenting the sequence of operations in a biophilic biofeedback session.

Referring now to FIG. 4, there will be described the sequence of operations in a biophilic biofeedback session. A user first selects one or more physiology parameter monitoring devices, such as hand temperature (HT), skin conductance level (SCL), heart rate variability (HRV), surface EMG (sEMG) (box 180). The decision is made (diamond 190) whether or not the user's operating characteristics curves (OCC) are available for the selected physiology monitoring device.

Each individual has a different operating characteristics curve (OCC) for a given physiology measure. For example, though hand temperature usually has a three regions, a slow initial region, a fast rising middle region and a slow end region, the rate of change and range of these regions vary from individual to individual. Also, the amount of efforts needed in each region vary from person to person. In certain regions, the user may have to receive some positive feedback (such as opening of the flower a tidbit to get them out of the valley). The time lapse or any feedback loop image should hence be able to have variable rate of change. The sequence can play forward or backward to match the individual's response.

The OCC for an individual can be understood through situation specific events such as baseline, a calming or relaxing session using other techniques, an activation session using still image etc. These OCC's can then be mapped to the range of the time lapse image.

If the decision is no, the user's OCC for the selected physiology device or devices is measured and recorded (box 200). If the decision is yes, the user selects a biophilic image sequence for the desired physiological effect, such as calming, relaxing, or activating (box 210). The selected image sequence is calibrated to the user's OCC (box 220). The user then selects optional audiovisual verbal coaching sounds, visual status indicators (box 230).

The user initiates the biofeedback session (box 240).

During the session, the decision is made (diamond 250) whether or not the user's physiological condition as measured by the monitoring device is changing toward the desired goal condition. If no, the rate of image sequence progression remains fixed and an image motion loop is initiated (box 260). If yes, the rate of image sequence progression changes relative to the rate of measured physiological change (box 270).

The goal physiological condition as measured by the monitoring devices is reached (box 280) and the biofeedback session is concluded (box 290).

All time lapse images are not the same. The characteristics of these images such as range, speed, rate of change possible is very important to make them suitable for different physiology measures.

Using image classification scheme disclosed in U.S. patent application, Ser. No. 09/430,580, the best time lapse images can be selected for each individual. For example, if an individual prefers landscapes and up/down motion for activation, we can then pick an image that allow the user to raise into the image.

The time lapse image range can also be increased by manipulating the image quality features along with the content. For example, let's take a flower opening scene. The close flowers could be less saturated, as the temperature increases, the flower open a little, start adding saturation, opens a little more... and after completely opening, the sharpness or contrast on the image changes. This allows an increased range to map the image to the physiology.

The image should also be able to show some background motion so that at any point the image does not look completely stagnant.

The invention has been described in detail with particular reference to certain preferred embodiments thereof, but it will be understood that variations and modifications can be effected within the spirit and scope of the invention.

PARTS LIST

| | |
|---|---|
| 10 | user |
| 20 | computer |
| 30 | computer monitor |
| 40 | physiology monitoring device |
| 50 | computer monitor image |
| 60 | image of a closed flower bud |
| 70 | image of flower buds 20% open |
| 80 | image of flower buds 40% open |
| 90 | image of flower buds 60% open |
| 100 | image of flower buds 80% open |
| 110 | image of flowers in full bloom |
| 120 | image of partially opened flowers leaning toward the right of the frame |
| 130 | image of partially opened flowers in the middle of the frame |
| 140 | image of partially opened flowers leaning toward the left side of the frame |
| 150 | image of partially opened flowers leaning toward the far left side of the frame |
| 160 | image of partially opened flowers back in the middle of the frame |
| 170 | image of partially opened flowers back leaning toward the right of the frame |
| 180 | user device selection step |
| 190 | calibration check decision step |
| 200 | calibration profile step |
| 210 | user image sequence selection step |
| 220 | selected image sequence calibrated user's profile step |
| 230 | user audio visual option selection step |
| 240 | session initiation step |
| 250 | measurement compared to profile decision step |
| 260 | motion loop step |
| 270 | image change step |
| 280 | goal state achieved step |
| 290 | session concluded step |

What is claimed is:

1. An apparatus for managing the physiological and/or psychological state of an individual comprising;
   a source of biophilic images;
   a device for sensing at least one physiological parameter of an individual; and
   a display, linked to said source and said device, for displaying biophilic images from said source as a function of the sensed physiological parameter in order to manage a physiological or psychological state of the individual wherein said device and said displayed biophilic images are selected and controlled by the individual to manage the individual's physiological and psychological state.

2. The apparatus of claim 1 wherein said source is a source of at least one of the following types of biophilic images;
   flowers budding and blooming;
   flowers budding, blooming and dying;
   the surface of a body of water progressing from rippled to still;
   waves dissipating until a body of water becomes still;
   rain falling on a body of water decreases in intensity until the water becomes still;
   a contained fire with increasing or decreasing intensity;
   clouds dissipating or forming in the sky.

3. The apparatus of claim 1 wherein said source is a source of digital biophilic images and said display is an electronic display linked to said source.

4. The apparatus of claim 1 wherein said display is an electronic display.

5. The apparatus of claim 1 wherein said display is a screen for receiving projected images from a film projector or an electronic image projector.

6. The apparatus of claim 1 wherein said device for sensing senses one or more of the following physiological parameters:
   body temperature (peripheral, core), heart rate, blood pressure, skin conductance response, brain waves, electromyography, eye saccades, etc.

7. The apparatus of claim 1 wherein said biophilic images are displayed on said display in a time lapse mode.

8. A method for an individual to manage physiological and/or psychological state of said individual comprising:
   first selecting by an individual one or more physiology monitoring devices;
   determining whether the individual's operating characteristic curve (OCC) is available for each selected physiology monitoring, and, if it is not, measuring and recording the individual's OCC for the selected device(s);
   second selecting, by said individual, a sequence of biophilic images to be displayed to said individuals;
   calibrating the selected image sequence to said individual's OCC for each said device;
   displaying said selected sequence of biophilic images to said individual;
   determining whether said individual's physiological condition as measured by said monitoring device(s) is changing toward a desired goal, physiological condition; and
   when the desired goal physiological condition is reached, concluding display of said images.

9. The method of claim 8 wherein said physiology monitoring devices include devices for monitoring one or more of the following physiological parameters;
   body temperature (peripheral, core), heart rate, blood pressure, skin conductance response, brain waves, electromyography, eye saccades, etc.

10. The method of claim 8 wherein said sequence of biophilic images include at least one of the following types of biophilic images:
    flowers budding and blooming;
    flowers budding, blooming, dying;
    the surface of a body of water progressing from ripples to still;
    rain falling on a body of water decreases in intensity until the water becomes still;
    a contained fire with increasing or decreasing intensity;
    clouds dissipating or forming in the sky.

11. The method of claim 8 including;
    third selecting by said individual of optional audio/visual verbal coaching, sounds, visual status indicators before said displaying said selected sequence of biophilic images.

12. The method of claim 8 wherein if, in said determining, said individual's physiological condition is not changing toward said desired goal physiological condition, the rate of image sequence progression remains fixed and an image motion loop is initiated.

13. The method of claim 12 wherein if said individual's physiological condition is changing toward said desired goal physiological condition, the rate of image sequence progression is changed relative to the rate of measured physiological change.

* * * * *